United States Patent
Warner et al.

(10) Patent No.: US 11,918,779 B2
(45) Date of Patent: Mar. 5, 2024

(54) SMART 1TOUCH

(71) Applicant: 1TOUCH Holdings Inc, Farmington Hartford, CT (US)

(72) Inventors: Jim Warner, Chicago, IL (US); Judith Grupp, Farmington, CT (US)

(73) Assignee: 1TOUCH HOLDINGS INC, Hartford, CT (US)

( * ) Notice: Subject to any disclaimer, the term of this patent is extended or adjusted under 35 U.S.C. 154(b) by 0 days.

(21) Appl. No.: 17/543,352

(22) Filed: Dec. 6, 2021

(65) Prior Publication Data

US 2022/0088292 A1    Mar. 24, 2022

Related U.S. Application Data

(63) Continuation-in-part of application No. 16/507,000, filed on Jul. 9, 2019, now Pat. No. 11,192,705.
(Continued)

(51) Int. Cl.
*A61M 5/148* (2006.01)
*A61J 1/10* (2006.01)
(Continued)

(52) U.S. Cl.
CPC .............. *A61M 5/148* (2013.01); *A61J 1/10* (2013.01); *A61J 1/1431* (2015.05); *A61J 1/1437* (2013.01);
(Continued)

(58) Field of Classification Search
CPC .......... A61M 5/148; A61M 2205/3303; A61M 2205/3331; A61M 2205/502; A61M 2205/3553; A61M 2205/3561; A61M 2205/3584; A61M 2205/6009; A61M 2205/6054; A61J 2200/30; A61J 1/1437; A61J 1/1475; A61J 7/0076; A61J 2200/70;
(Continued)

(56) References Cited

U.S. PATENT DOCUMENTS 6,053,888 A    4/2000   Kong
6,790,198 B1   9/2004   White et al.
(Continued)

FOREIGN PATENT DOCUMENTS

WO     2016155970 A1    10/2016

OTHER PUBLICATIONS

Chinese Office Action; dated Feb. 7, 2022; Application No. 201980041498.7; Filed: Jul. 9, 2019; 13 pages.
(Continued)

*Primary Examiner* — Frederick C Nicolas
(74) *Attorney, Agent, or Firm* — CANTOR COLBURN LLP

(57) ABSTRACT

An apparatus and method of using a device for dispensing fluid having a flexible and collapsible container, a fluid dispenser pump connected to the flexible and collapsible fluid container configured to draw fluid from the flexible and collapsible fluid container into the fluid dispenser pump and to dispense fluid through a fluid delivery channel to an exit port upon actuation of the pump; and the dispenser pump having an actuator that has a dose delivery button, and a sensor located in the apparatus and configured to actuate the dispenser pump upon physical contact of the dose delivery button by a user.

21 Claims, 17 Drawing Sheets

Related U.S. Application Data

(60) Provisional application No. 62/695,306, filed on Jul. 9, 2018.

(51) Int. Cl.
  *A61J 1/14* (2023.01)
  *A61J 7/00* (2006.01)
  *B05B 11/10* (2023.01)
  B05B 11/02 (2023.01)
  G01F 13/00 (2006.01)

(52) U.S. Cl.
  CPC ........... *A61J 1/1475* (2013.01); *A61J 7/0076* (2013.01); *B05B 11/1008* (2023.01); *B05B 11/1032* (2023.01); A61J 2200/30 (2013.01); A61J 2200/70 (2013.01); A61J 2205/60 (2013.01); A61M 2205/3303 (2013.01); A61M 2205/3331 (2013.01); A61M 2205/3553 (2013.01); A61M 2205/3561 (2013.01); A61M 2205/3584 (2013.01); A61M 2205/502 (2013.01); A61M 2205/6009 (2013.01); A61M 2205/6054 (2013.01); B05B 11/026 (2023.01); G01F 13/008 (2013.01)

(58) Field of Classification Search
  CPC ........ A61J 2205/60; A61J 1/1431; A61J 1/10; G01F 13/008; B05B 11/3008; B05B 11/3032; B05B 11/00412; B05B 11/1008; B05B 11/1032; B05B 11/026
  See application file for complete search history.

(56) References Cited

U.S. PATENT DOCUMENTS

| | | | |
|---|---|---|---|
| 8,287,495 B2* | 10/2012 | Michaud | A61M 5/172 604/152 |
| 10,259,645 B2* | 4/2019 | LaFlamme | G01F 11/288 |
| 11,311,808 B2* | 4/2022 | Schwartz | A63F 13/816 |
| 11,369,761 B2* | 6/2022 | Tritschler | A61M 11/006 |
| 2010/0176151 A1* | 7/2010 | Johnson | B65D 77/067 222/542 |
| 2010/0214106 A1 | 8/2010 | Braun | |
| 2012/0029433 A1 | 2/2012 | Michaud et al. | |
| 2016/0213565 A1 | 7/2016 | Kijowski et al. | |
| 2017/0334632 A1 | 11/2017 | Laflamme et al. | |

OTHER PUBLICATIONS

Chinese Office Action; dated Aug. 29, 2022; Application No. 201980041498.7; Filed: Jul. 9, 2019; 23 pages.
European Search Report; dated Mar. 9, 2022; Application No. 19833812.1; Filed: Jul. 9, 2019; 10 pages.
International Search Report and Written Opinion for International Application No. PCT/US/1941090; International Filing Date: Jul. 9, 2019; dated Oct. 29, 2019; 7 pages.
Japanese Office Action; dated Dec. 12, 2022; Application No. 2021-523562; Filed: Jul. 7, 2019; 4 pages.

* cited by examiner

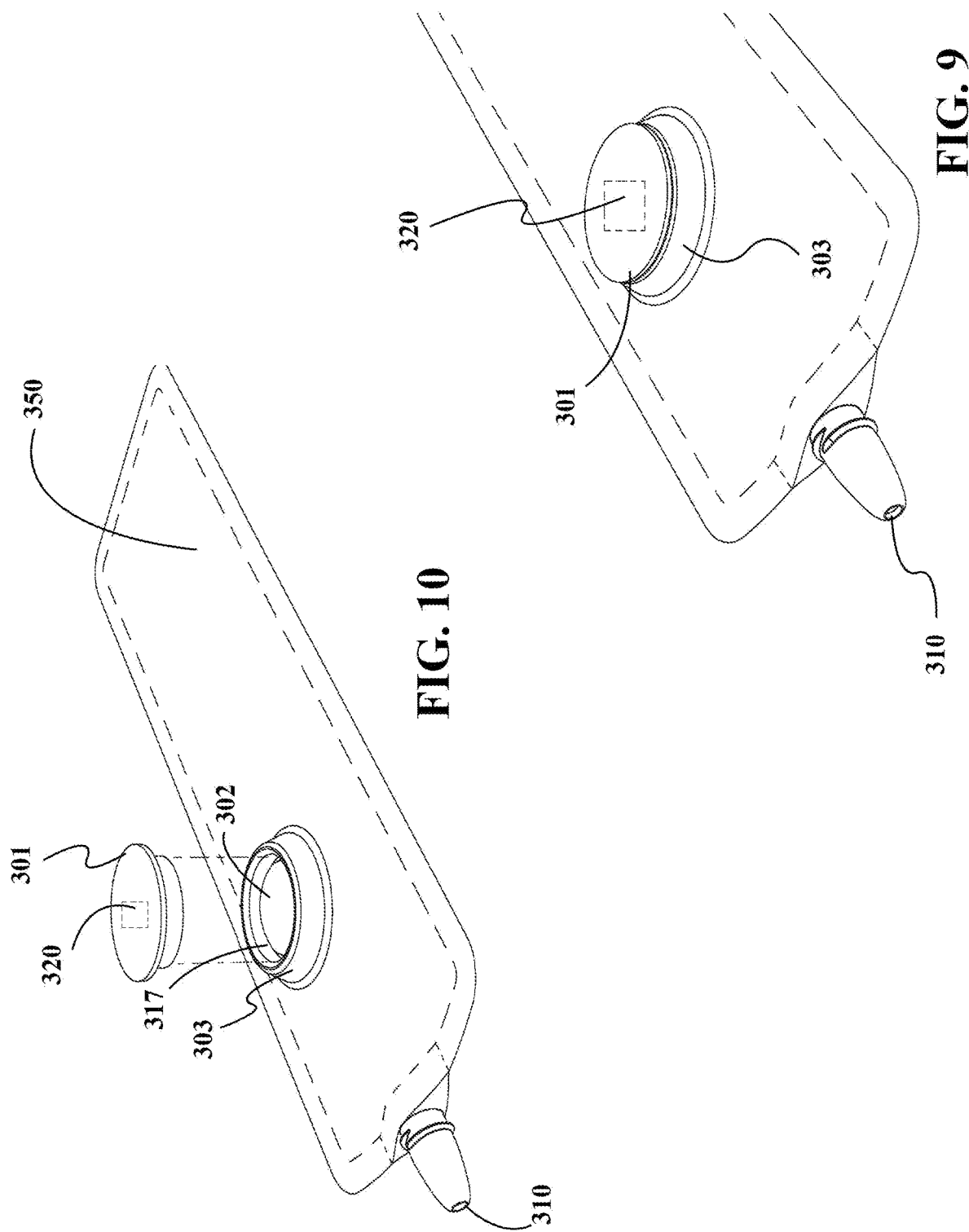

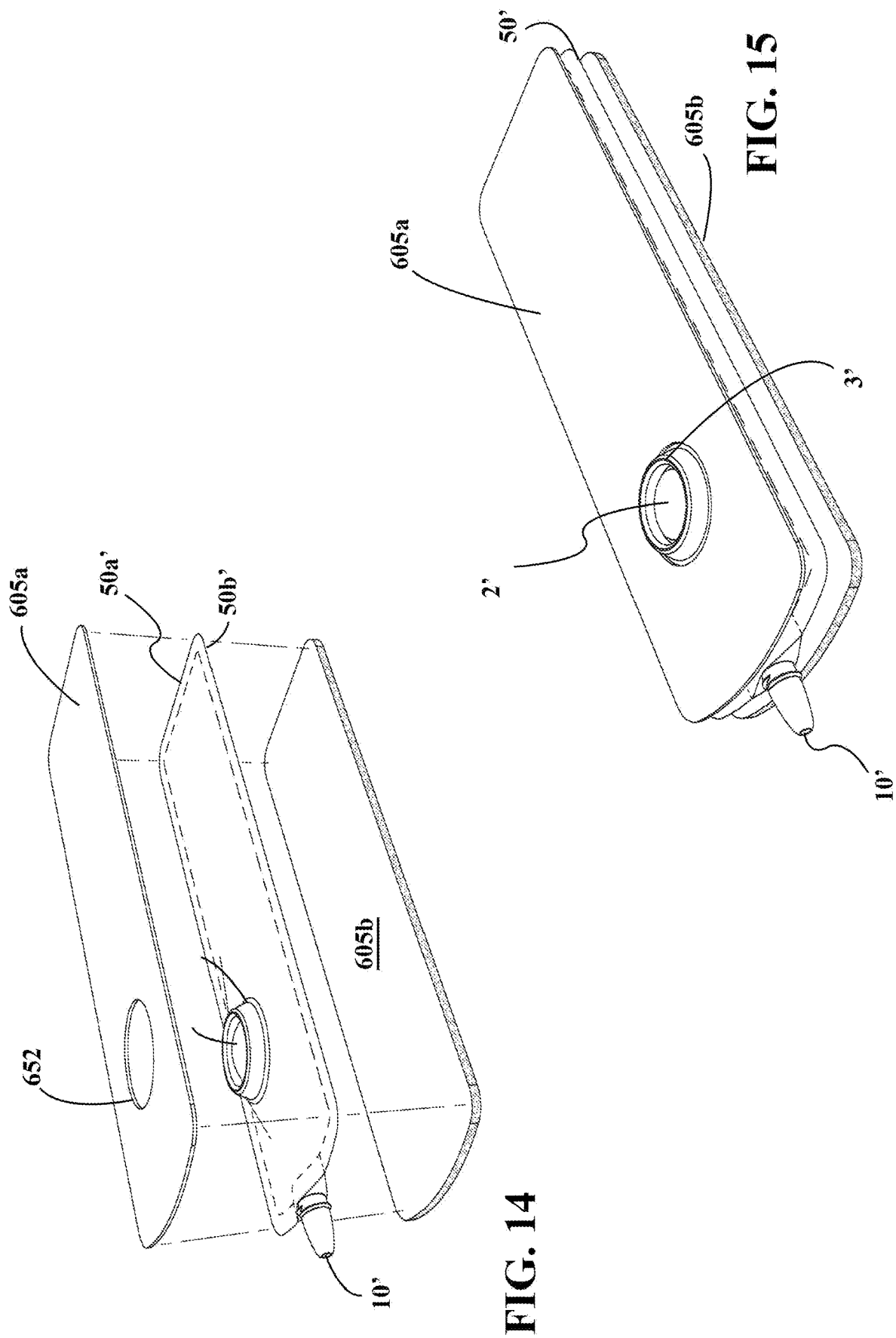

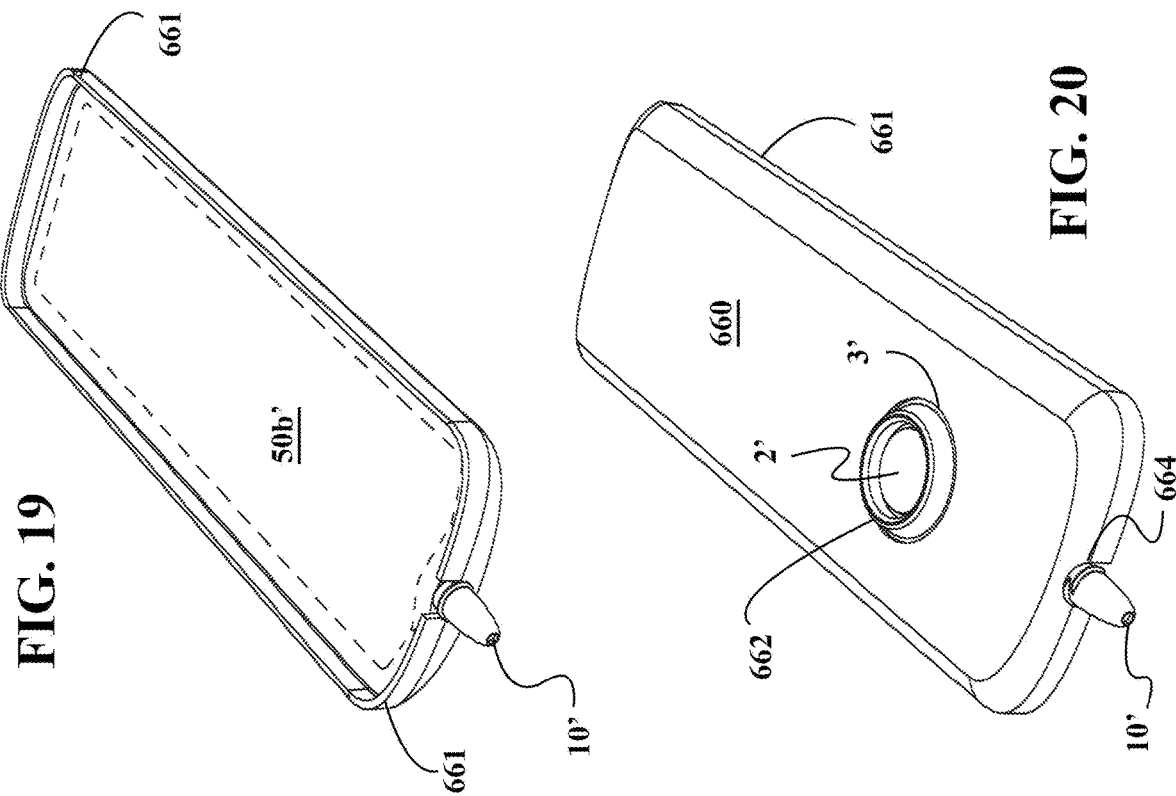
FIG. 19
FIG. 20
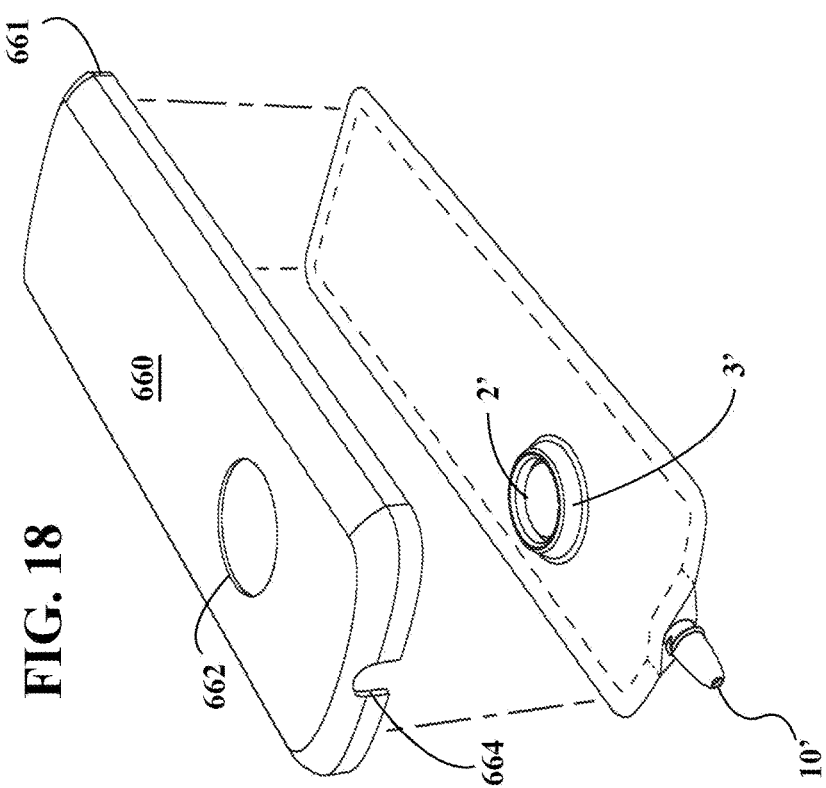
FIG. 18

SMART 1TOUCH

CROSS REFERENCE TO RELATED APPLICATIONS

This application is a continuation-in-part of U.S. application Ser. No. 16/507,000 filed Jul. 9, 2019, which claims the benefit of U.S. Provisional Application No. 62/695,306 filed Jul. 9, 2018, which are incorporated herein by reference in their entirety.

BACKGROUND OF THE INVENTION

1. Field of the Invention

The present invention relates to methods and devices for accurate dispensing, tracking, and reordering of dispensed fluids.

2. Description of Related Art

The technical problems solved by the present invention are: the delivery of information to users of fluids, ensuring that users of fluids use an accurate measurement(s) at the specified time, GPS location of fluid dispensing activity, accurate tracking of the time and dose, enable reminders for use and amount of the dosage to prevent overdose and to track compliance, and prompt for reorder to ensure ongoing compliance for which there is no current solution available, and communication of tracking information to the user, physicians, health care providers, retailers, manufacturers and others who wish to monitor usage, manage compliance, and reorder the fluid. Smart 1 TOUCH will integrate to electronic data collection, smart devices and audible data devices.

SUMMARY OF THE INVENTION

The present invention solves the technical problems described above by either combining a mechanical measured fluid dispenser or sensor technology, such as Bluetooth or RFID, with hardware and software features that detect the time and amount of a fluid dispensing operation, and communicate that information to a user's smart phone app or software which can then optionally, and preferably according to a user-selection, communicate that information to the user's physician, pharmacy, retailers, manufacturers or other interested parties requiring compliance, monitoring and reordering capabilities.

According to various embodiments of the invention, the mechanical or sensor based measured fluid dispenser of the type disclosed in, for example, U.S. Pat. Nos. 8,123,073, 7,419,322, 8,387,833, 10,259,645 and/or in U.S. patent application Ser. No. 15/941,893, the disclosures of which are incorporated herein in their entirety.

According to further embodiments of the invention, the sensor or mechanical measured fluid dispenser may include a chip or other sensor configured to detecting a physical change caused by the depression of the dispenser's actuator. For example, the sensor may be a pressure sensor, or a flow rate sensor, a timer, or some combination thereof. The sensor may be any single sensor or combination of sensors that provide information concerning the amount of fluid that is dispensed upon the activation of the dispenser's actuator. Accordingly, the sensor may be located inside or beneath the actuator itself, located somewhere in the fluid channel/pathway, or in dispenser case enclosures.

According to another embodiment, the mechanical measured dispenser may include an adjustable dose mechanism according to which the amount of the dose may be adjusted by the user. According to a further feature of this embodiment, one or more sensors may be provided to determine the adjustment state of the adjustable dose feature. According to one embodiment, the sensor that determines the adjustment state of the adjustable dose mechanism may be separate from and optionally in addition to the sensors) that detects and/or measures the amount of a dose when the dose actuator is actuated.

According to a further embodiment, the measured dosing device may be reusable, according to which it may be removed from a first fluid pouch when the first fluid pouch is empty and attached to a second fluid pouch with a fresh supply of fluid.

According to further embodiments, the fluid pouches may include a smart label and/or RFID tag. According to aspects of these embodiments, a user may scan the smart label or RFID tag with a smart phone app which would then cause information concerning the fluid to be displayed to the user. Such information might include how to administer the fluid by using the mechanical measured dispenser or pouch dispenser, how to use the app remind the user to administer the fluid, track compliance, location of where to reorder, automatically reorder, or identify location where fluid can be obtained, how to use the app to track transmit dosage and time information and/or to transmit such information to interested parties, according to the user's preferences and selections.

In another embodiment, the present invention may be directed to an apparatus and method for dispensing fluid comprising a flexible and collapsible fluid container, a fluid dispenser pump connected to the flexible and collapsible fluid container configured to draw fluid from the flexible and collapsible fluid container into the fluid dispenser pump and to dispense fluid through a fluid delivery channel to an exit port upon actuation of the pump, the dispenser pump having an actuator comprising a dose delivery button, and a sensor located in the apparatus and configured to actuate the dispenser pump upon physical contact of the dose delivery button by a user. The method of using comprises providing the fluid dispensing apparatus, contacting by the user the dose delivery button, signaling the sensor to actuate the fluid dispensing pump, and dispensing fluid from the fluid container through the exit port.

In a further embodiment, the present invention may be directed to an apparatus and method of using a fluid dispensing device comprising a generally cylindrical base unit having a generally flat and continuous bottom surface, a top surface having a raised circumferential wall, and a center area, a flexible dosing dome configured to sit inside the center area of the base unit to form a pump chamber, the bottom surface of the base unit having a fluid inlet opening to the pump chamber to permit the flow of fluid therethrough, the base also defining a fluid delivery channel between the pump chamber and a fluid delivery outlet opening on an outside surface of the base unit, a combination dial and button having the shape of a cylinder with a closed top and open bottom, a bottom portion of the combination dial and button configured to sit inside a channel defined by the base unit top surface and the flexible dome, said button including a Graphical User Interface in communication with a sensor to adjust by a user an amount of a dose of fluid to be dispensed, the sensor located in the device and further configured to actuate the pump chamber upon physical contact of the dose delivery button by the user. The method comprises providing the fluid dispensing device described above, selecting from the Graphical User User Interface on the button by the user the adjustment state of the actuator, signaling to the sensor the adjustment state of the actuator to adjust the amount of the dose of fluid dispensed upon actuation, contacting, by the user, the dose delivery button to send a signal to the sensor, and signaling actuation of the pump chamber by the sensor upon contact of the button, wherein the pump chamber dispenses the selected dose of fluid to the outside surface of the base unit.

Yet another embodiment of the present invention may be directed to an apparatus and method for dispensing and monitoring fluid dispensed comprising a flexible fluid container, a fluid dispenser pump connected to the flexible and collapsible fluid container configured to draw fluid from the flexible and collapsible fluid container into the fluid dispenser pump and to dispense fluid through a fluid delivery channel to an exit port upon actuation of the pump, a sensor located in the apparatus and configured to actuate the dispenser pump upon a first voice command received by the sensor by a user, the sensor further configured to measure a physical change upon receipt of a second voice command by the user, the physical change comprising information on the amount of fluid dispensed, and a wireless transmission module in communication with the sensor configured to communicate a physical change to a remote device upon receipt of the second voice command by the user. The method of dispensing and monitoring fluid dispensed comprises providing the fluid dispensing device described above, signaling by the user to the sensor the first voice command or the second voice command, wherein the sensor signals actuation of the fluid dispenser pump to dispense the fluid from the flexible and collapsible fluid container through the exit port in response to receiving the first voice command, and wherein the sensor wirelessly transmits information on the amount of fluid dispensed from the sensor to a remote device in response to receiving the second voice command by the end user.

Still another embodiment of the present invention may be directed to an apparatus and method for dispensing and adjusting an amount of fluid dispensed. The apparatus comprises a flexible and collapsible fluid container, a fluid dispenser pump connected to the flexible and collapsible fluid container configured to draw fluid from the flexible and collapsible fluid container into the fluid dispenser pump and to dispense fluid through a fluid delivery channel to an exit port upon actuation of the pump, and a sensor located in the apparatus apparatus and configured to actuate the dispenser pump upon a first voice command received by the sensor by a user, the sensor further configure to adjust an amount of a dose of fluid to be dispensed upon receipt of a second voice command by the user. The method comprises providing the fluid dispensing apparatus described above, signaling by the user to the sensor the first voice command or the second voice command, wherein the sensor signals actuation of the fluid dispenser pump to dispense the fluid from the flexible and collapsible fluid container through the exit port in response to receiving the first voice command by the end user, and wherein the sensor to adjusts an amount of a dose of fluid to be dispensed in response to receiving the second voice command by the end user.

Another embodiment of the present invention may be directed to an apparatus comprising a flexible and collapsible fluid container, a fluid dispenser pump connected to the flexible and collapsible fluid container configured to draw fluid from the flexible and collapsible fluid container into the fluid dispenser pump and to dispense fluid through a fluid delivery channel to an exit port upon actuation of the pump, and a biometric sensor located in the apparatus and configured to unlock actuation of the dispenser pump upon biometric identification information received by the sensor, the sensor further configure to unlock adjustment of an amount of a dose of fluid to be dispensed by the fluid dispenser pump upon biometric identification information received by the sensor. The method of unlocking the apparatus comprises providing the apparatus described above, detecting biometric identification information by the sensor, analyzing the biometric identification information to detect an initial biometric identification information, and in response to detecting the initial biometric identification information, allowing a user of the fluid dispensing device to actuate the fluid dispenser pump to dispense the fluid from the flexible and collapsible fluid container through the exit port, adjust the amount of the dose of fluid to be dispensed by said fluid dispenser pump, or both.

A further embodiment of the present invention may be directed to an apparatus for dispensing and monitoring fluid dispensed comprising a flexible and collapsible fluid container, a fluid dispenser pump connected to the flexible and collapsible fluid container configured to draw fluid from the flexible and collapsible fluid container into the fluid dispenser pump and to dispense fluid through a fluid delivery channel to an exit port upon actuation of the pump, the dispenser pump having an actuator comprising a dose delivery button which, upon depression by a user, actuates the fluid dispenser pump to dispense a dose of fluid, a flexible cover secured to an exterior surface of the container, wherein the flexible cover is of dimensions similar to dimensions of the container to protect the container, and wherein the flexible cover constructed of materials which are environmentally sustainable, a sensor located in the apparatus and configured to measure a physical change upon depression of the dose delivery button of the fluid dispenser pump by a user, the physical change comprising information on the amount of fluid dispensed, a wireless transmission module in communication with the sensor configured to communicate the physical change to a remote device depression of the dose delivery button of the fluid dispenser pump by the user, wherein the wireless transmission module communicates the physical change to the remote device only upon depression of the dose delivery button. The method comprises providing the flexible cover and dispensing device described above, and securing the flexible cover to an exterior surface of the container such that the flexible cover provides a protective surface to the container.

Another embodiment of the present invention may be directed to an apparatus for dispensing and monitoring fluid dispensed comprising a flexible and collapsible fluid container, a fluid dispenser pump connected to the flexible and collapsible fluid container configured to draw fluid from the flexible and collapsible fluid container into the fluid dispenser pump and to dispense fluid through a fluid delivery channel to an exit port upon actuation of the pump, the dispenser pump having an actuator, and a cover secured to an exterior surface of the container, wherein the cover is of dimensions similar to dimensions of the container, the cover including sidewalls around a periphery of the flexible cover to encase the container therein, the cover constructed of materials which are environmentally sustainable, wherein the sidewalls of the cover include a flat end such that the container may be placed on an end thereof while on a substantially flat surface. The method comprises providing the cover and dispensing device described above, and securing the cover to an exterior surface of the container such that the flexible cover provides a protective surface to the container.

Yet another embodiment of the present invention may be directed to an apparatus for dispensing and monitoring fluid dispensed comprising a flexible and collapsible fluid container, a fluid dispenser pump connected to the flexible and collapsible fluid container configured to draw fluid from the flexible and collapsible fluid container into the fluid dispenser pump and to dispense fluid through a fluid delivery channel to an exit port upon actuation of the pump, the dispenser pump having an actuator which actuates the fluid dispenser pump to dispense a dose of fluid, a sensor located in the apparatus and configured to measure a physical change upon actuation of the fluid dispenser pump by a user, the physical change comprising information on the amount of fluid dispensed, and a wireless transmission module in communication with the sensor configured to communicate the physical change to a remote device upon actuation of the fluid dispenser pump by the user, wherein the wireless transmission module communicates the physical change to the remote device only upon depression of the dose delivery button, and wherein actuation of the dispensing pump provides the sensor with dose information including dose amount, time of day, or both to predict the dose information on a future actuation of the dispensing pump transmitted to the remote device by the wireless transmission module. The method comprises providing the fluid dispensing apparatus described above, actuating, by the user, the fluid dispenser pump to dispense the fluid from the flexible and collapsible fluid container through the exit port, upon actuation of the fluid dispenser pump, sensing by the sensor information on the amount of fluid dispensed from the exit port, storing the information on the amount of fluid dispensed from the exit port, determining suggested dose information in response to the information on the amount of fluid dispensed from the exit port stored by the sensor, and providing the suggested dose information to the remote device by the wireless transmission module.

Accordingly, the present invention provides a reliable and verifiable way for users of fluids to be automatically reminded to administer a dosage, for users to be sure that the appropriate dosage is being administered, and physician, pharmacy, retailers, manufacturers, or others requiring compliance, monitoring and reordering capabilities can reliably track and document usage.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

FIG. 1b is an alternate rendition of the embodiment shown in FIG. 1a.

FIG. 2 is a bottom perspective view of the dosing/control collar shown in FIG. 1a.

FIG. 3 is a cross-sectional view of the dosing/control collar shown in FIG. 1a.

FIG. 5b is an alternate rendition of the embodiment shown in FIG. 5a.

FIG. 6b is a side elevation view of the adjustable fluid dosing dispenser according to the embodiment of FIG. 6a.

FIG. 7b is an alternate rendition of the embodiment shown in FIG. 7a.

FIG. 8b is an alternate rendition of the embodiment shown in FIG. 8a.

FIG. 9 is a partial perspective view of an embodiment of the fluid dispensing device of the present invention.

FIG. 10 is a perspective, partially exploded view of an embodiment of the fluid dispensing device of the present invention.

FIG. 14 is an exploded view of an embodiment of the fluid dispensing device of the present invention.

FIG. 15 is a perspective view of an embodiment of the fluid dispensing device of the present invention.

FIG. 18 is an exploded view of an embodiment of the fluid dispensing device of the present invention.

FIG. 19 is a bottom perspective view of the embodiment of the fluid dispensing device shown in FIG. 18.

FIG. 20 is a perspective view of the embodiment of the fluid dispensing device shown in FIG. 18.

DESCRIPTION OF THE EMBODIMENT(S)

Figure 1A:
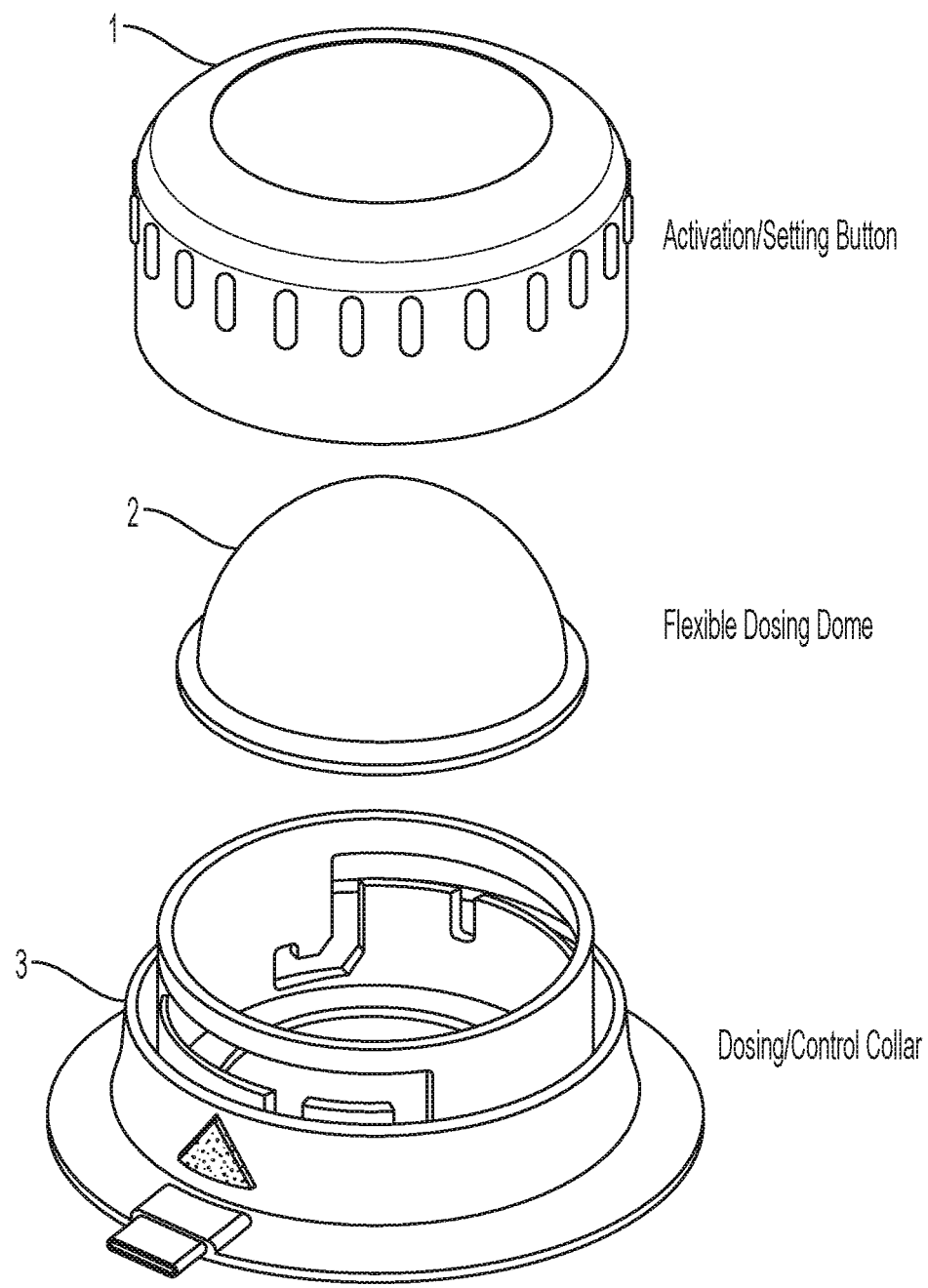
FIG. 1a is an exploded perspective view of an adjustable fluid dosing dispenser according to an embodiment of the invention.
Figure 1B:
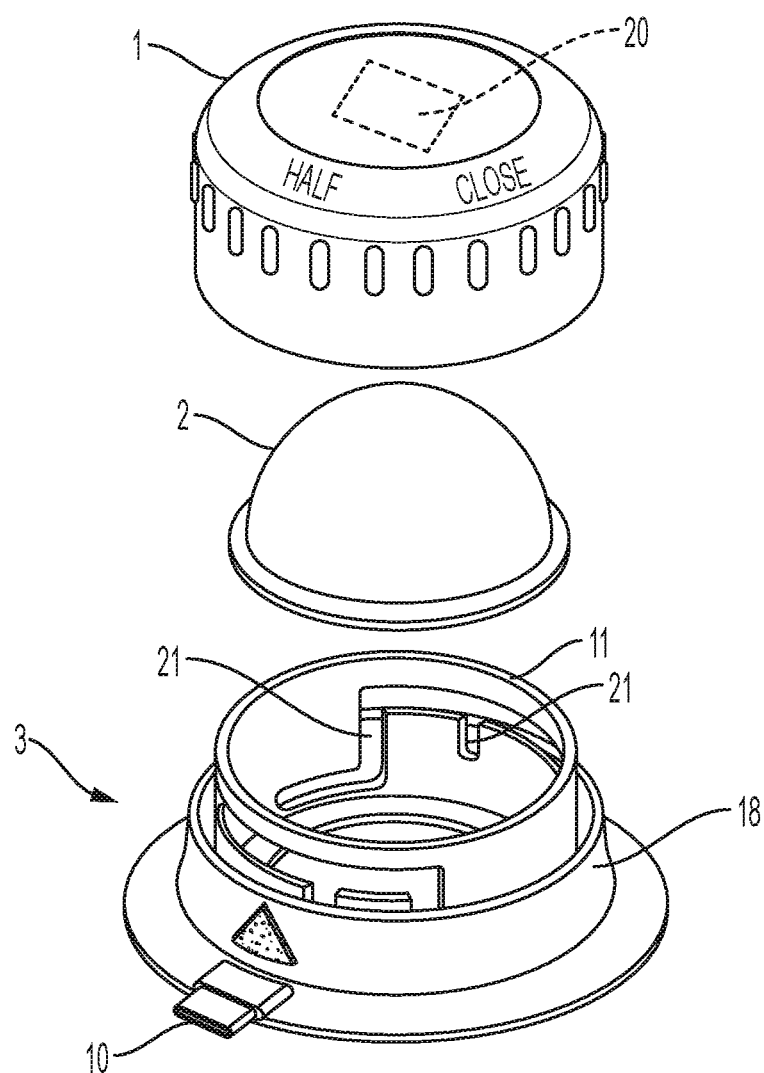
Figure 1C:
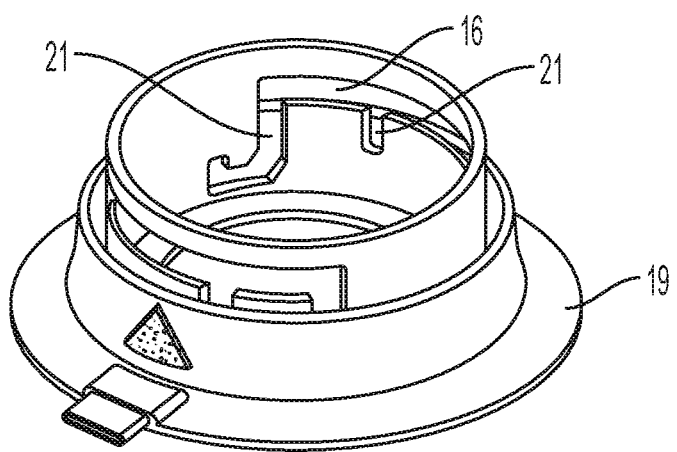
FIG. 1c is a perspective view of an adjustable fluid dosing dispenser dosing collar with an alternative slot design.
Figure 1D:
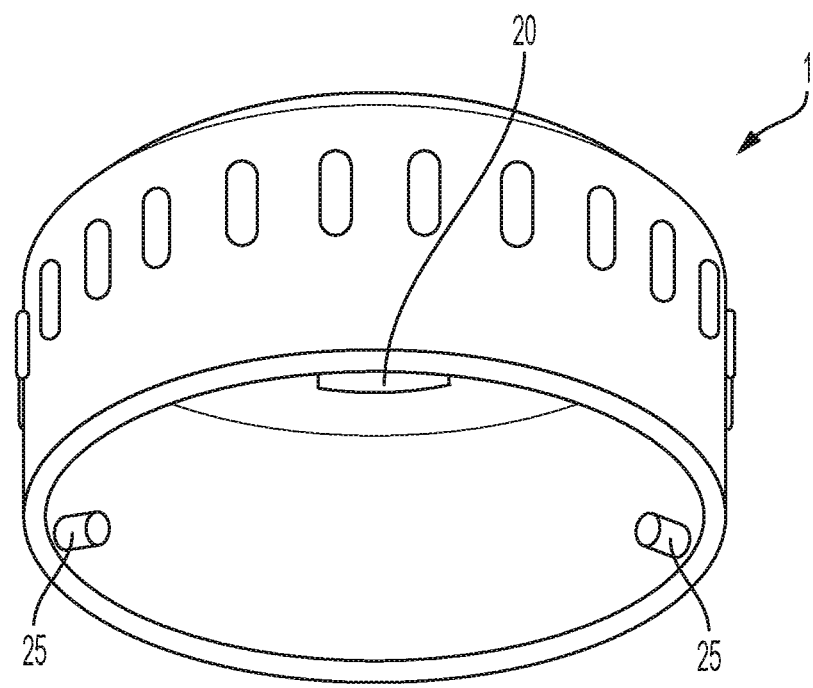
FIG. 1d is a bottom perspective view of the dosing dial/button.
Figure 2:
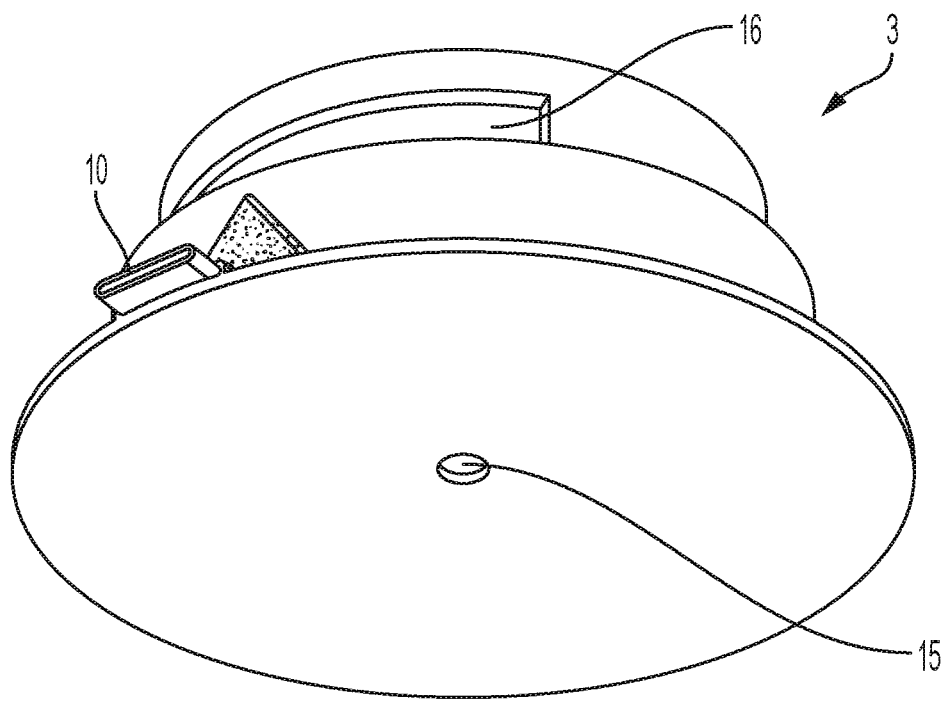

In describing the embodiment of the present invention, reference will be made herein to FIGS. 1-23 of the drawings in which like numerals refer to like features of the invention.

The present, invention is a device for dispensing fluid from a pouch, the device capable of being set to different discrete and repeatable/equal dispensing amounts, depending on the amount of fluid required to be dispensed by the user for various applications and uses. The device may also be set to an "off" or "closed" position to prevent accidental dispensing of fluid when not in use. The device is preferably configured to be affixed to the outer surface of a fluid container 50, which fluid container is preferably a flexible bag or pouch, though portions of dispensing device may be situated inside or outside the fluid container 50, provided that dosing dome 2 or button 1 is accessible from the outside of the flexible container for actuation by the user. According to various embodiments, at least one surface of the fluid container 50 or a sufficient portion of the fluid container 50 is flexible to allow the container to collapse as fluid is withdrawn therefrom. In the case that the entire fluid container 50 is not made of flexible material, the dispensing device is preferably attached to portion of the container 50 that is flexible and which is collapsible as fluid is dispensed from the container 50.

The device also includes one or more sensors 20 configured to record, store and/or transmit one or more physical properties of the device, particularly when the dispensing device is actuated in order to dispense fluid and/or when the device is adjusted to a particular dose.

FIGS. 1a-1e show an embodiment of the device including a dosing/control collar 3, a flexible dosing dome 2, and a combined dose setting dial and dose delivery button 1. The flexible dosing dome 2 and the dosing/control collar 3, when assembled, form the pump or dosing chamber. The dosing/control collar 3 is preferably cylindrical in shape with concentric inner and outer annular shafts/columns 11,18 rising from a common base and defining a narrow channel 17 between them. The exterior of the outer annular shaft 18 may feature a flange 19 that extends away from the center of the shaft. The interior shaft 11 also features a plurality of horizontal and vertical dosing and rotation channels or slots 21 that receive and interact with corresponding nubs on the outside surface of the dose dial/button 1. According to an alternative embodiment, the dosing and rotation channels may be on the shaft of the dose dial/button 1 and the nubs 25 may be on the outside surface of the inner annular shaft 11. The horizontal slots 16 are the rotation slots and may have a plurality of detente locations so that the user can tactically feel the progress of the dial as it is being rotated. The vertical channels 21 are the dosing slots and have differing depths (measured from the horizontal slot 16 to the bottom of the vertical slot) which correspond to different dispensing amounts. According to a preferred embodiment, each vertical slot 21 in the inner annular shaft 11 is paired with a second vertical slot 21 of the same depth, spaced apart on the inner annular shaft 11, and each nub 25 on the dose dial/button 1 is paired with a second nub 25 spaced apart on the dose dial/button 1 at a location that corresponds to the location of the second vertical shaft 21. When the dial/button 1 is rotated so that a nub 25 on the exterior of the dial/button 1 lines up with a vertical slot 21, the button 1 can be depressed to dispense fluid. The limit of depression limits the amount dispensed, and the depth of the vertical slot 21 limits how far the button 1 can be depressed because when the nub 25 hits the bottom of the vertical slot 21, the dial/button 1 is prevented from being depressed any further without breaking the nub 25, the slot/channel 21, or both.

According to one embodiment, there is at least one vertical slot or set of vertical slots 21 for a "Full" dose, and there is at least one second vertical slot or set of vertical slots 21 for a "Half" or "Partial" dose. According to other embodiments, there may be a third and fourth vertical slots or sets of vertical slots 21 for other fractional doses, for example, ¾ dose, ⅔ dose, ⅓ dose and ¼ dose.

Figure 3:
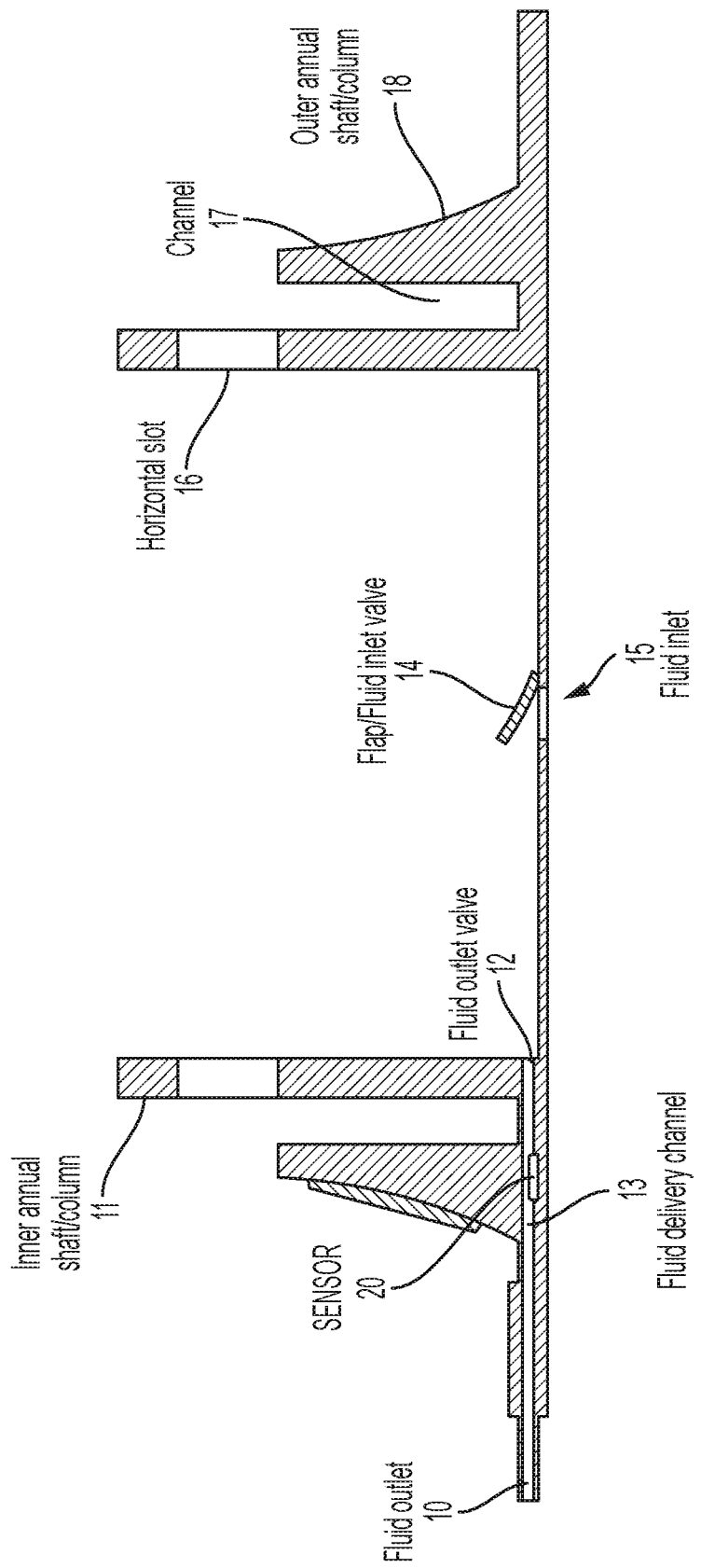

The dosing control collar 3 also features a through-opening 15 in the bottom surface to accommodate the entry of fluid, fluid inlet valve 14, represented in FIG. 3 as a flexible flap that is configured to lie over the through-opening, a fluid outlet 10 on the outside surface of the dosing control collar 3, and a fluid delivery channel 13 between said fluid inlet 15 and said fluid outlet 10.

Figure 4:
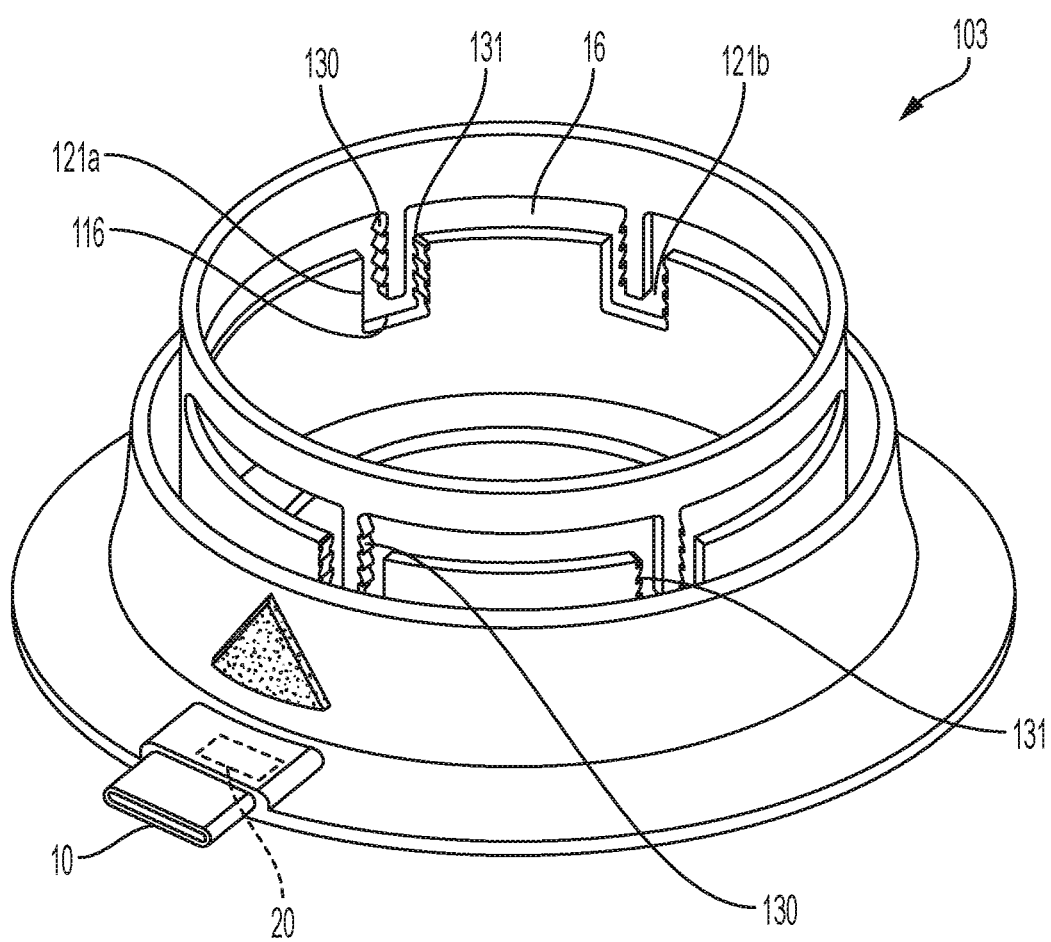
FIG. 4 is a perspective view of a dosing/control collar according to a further alternative embodiment of the invention.

According to a further alternative embodiment shown in FIG. 4, the dosing collar 3 may have separate dosing slots 121a and return slots 121b. According to this embodiment, the dosing slots 121a may have downward facing teeth or prongs 130 which prevent the nubs 25 from traveling upwards, thus requiring that the dial/button 1 be fully depressed before it returns to the set position. Since the nubs 25 cannot travel upwards in the dosing slots 121a, separate return slots 121b are provided adjacent the dosing slots, connected by a horizontal slot 116. The return slots 121b preferably have upward facing teeth or prongs 131 to prevent the nubs 25 from traveling downward while in the return slots 121b.

The dose setting dial/dose delivery button is preferably manufactured of relatively rigid plastic having a rigid bottom portion that snaps into the channel 17 formed between the inner and outer annular shafts 11,18 of the base (dosing/control collar 3).

The dose setting dial/dose delivery button 1 and the dosing/control collar 3 are preferably made of a rigid plastic material. Nubs 25 molded to or otherwise formed on the interior surface of the dial/button 1 rest inside the slots formed in the interior shaft 11. When a user presses the dial/button 1, the dial/button 1 forces the flexible dosing dome 2 downward to evacuate the interior volume of the dome 2 via the fluid outlet 10; when the dial/button 1 is released, the flexible dosing dome 2 returns to its original shape, forcing the dial/button 1 upward, and drawing fluid into the interior of the dome 2 under vacuum action.

The flexible dosing dome 2 is preferably made of shape memory elastomeric material that returns to its original shape after deformation.

Figure 5A:
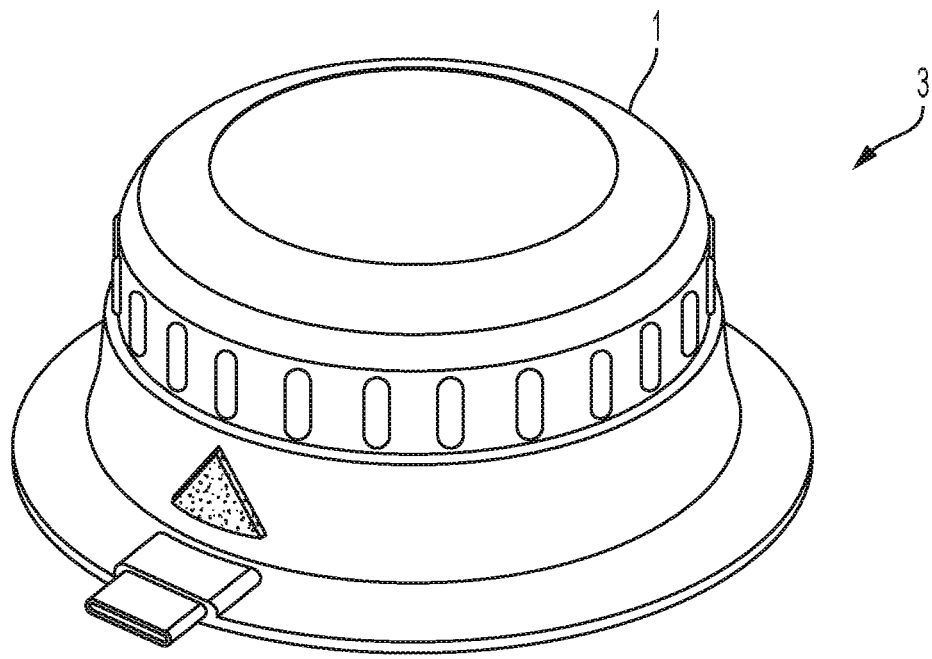
FIG. 5a is a perspective view of an assembled adjustable fluid dosing dispenser according to an embodiment of the invention in a closed/locked position.
Figure 5B:
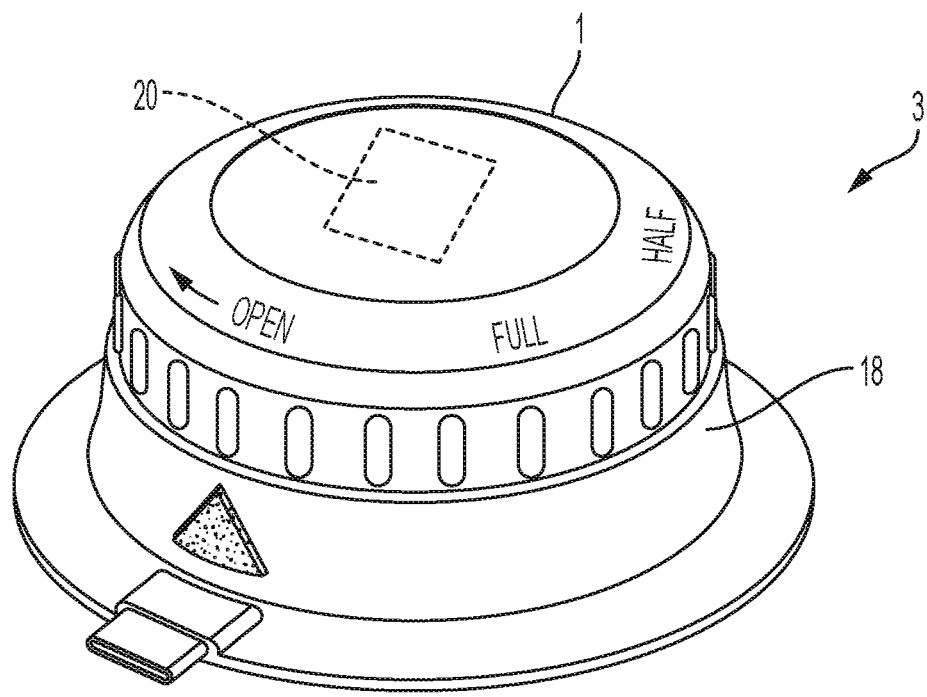

FIGS. 5a and 5b show these three parts assembled into an adjustable fluid dispensing device according to the invention in which the flexible dosing dome 2 is sealed to the base inside the interior column 11 of the dosing/control collar 3 and the bottom portion of the dose setting dial/dose delivery button 1 is snapped over the flexible dosing dome 2 into the channel 17 between the inner and outer shafts 11,18. The upper portion of the dial/button 1 projects above the top of the dosing/control collar 3. According to a preferred embodiment, the perimeter of the upper portion of the dial/button 1 has molded or printed indicia such as "Open" "Closed" and "FULL" and "HALF" to indicate the rotary position of the dial 1 that corresponds to various functions or dispensing amounts. Each of these indicia corresponds to a nub/slot combination that permits no depression, full depression, half depression, or other partial depression to dispense a corresponding amount of fluid.

Likewise, the outside surface of the outer shaft 18 of the collar 3 preferably has printed or molded or other indicia indicating the location on the collar 3 that must be lined up with the appropriate indicia on the dial/button 1 in order to achieve the desired function. In the configuration shown in FIGS. 5a and 5b, the dial/button 1 is in the fully depressed position, and rotated counterclockwise so that the nubs 25 on the inside surface of the dial/button 1 are in the bottom horizontal slot 30, locking the dial/button 1 into a closed position.

According to a preferred embodiment, the bottom horizontal slot 30 has a slight downward slant before becoming horizontal to draw the dial/button 1 down slightly as it is rotated into the closed position, see FIG. 1e, causing the bottom surface of the dial/button 1 to bear down on the fluid delivery channel 13, pinching it shut. As shown in FIGS. 5a and 5b, the indicia on the collar 3 lines up with a "<Open" indicia on the button 1, showing that in order to dispense fluid, the dial/button 1 must be rotated clockwise until the nubs line up with the "FULL" vertical slot. If the user wishes to dispense only a half dose, the dial/button 1 must be rotated clockwise again until the nubs 25 line up with the correspondingly shorter/shallower vertical channel/slot.

Figure 6A:
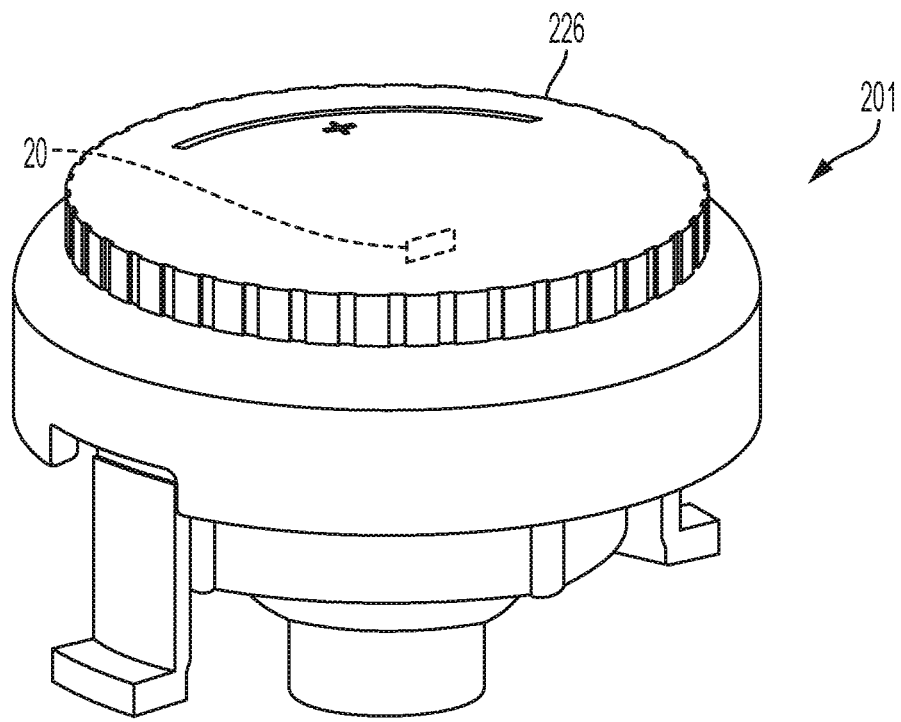
FIG. 6a is a perspective view of an adjustable fluid dosing dispenser according to another embodiment.
Figure 6B:
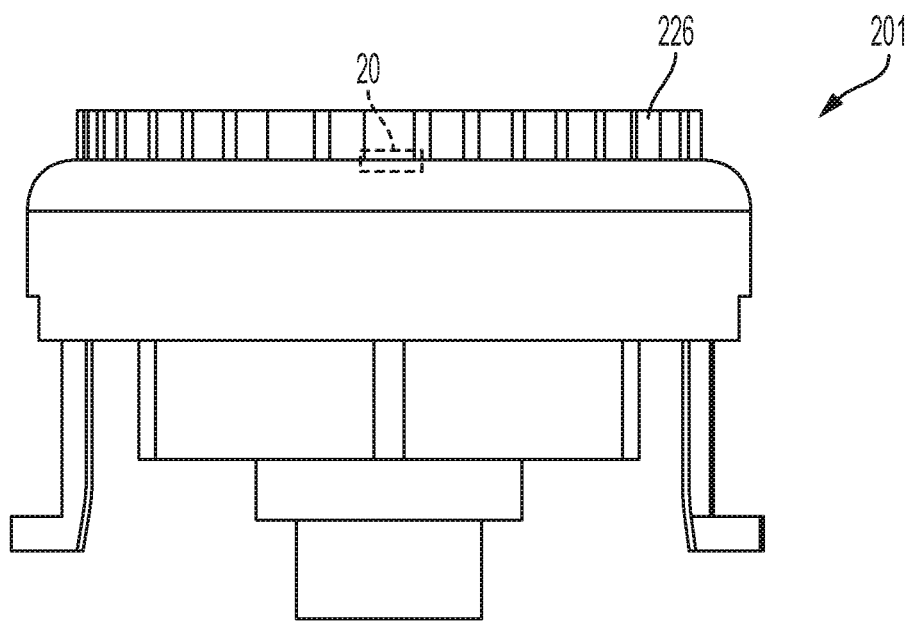
Figure 6C:
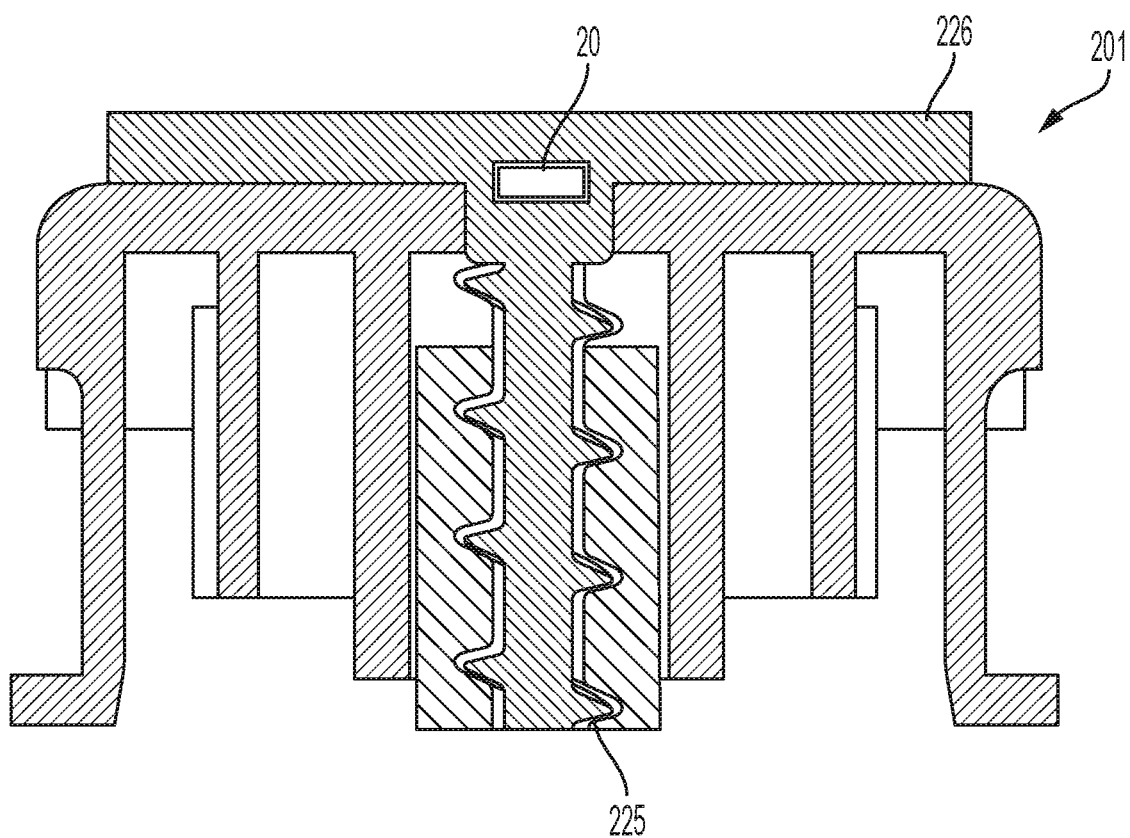
FIG. 6c is a side cross-sectional view of the adjustable fluid dosing dispenser according to the embodiments of FIGS. 6a and 6b.

FIGS. 6a, 6b and 6c show an alternative design of an adjustable fluid dispensing device according to the invention. Instead of the nub and slot interaction of the device shown in FIGS. 1a-1d, 2, 4, 5a and 5b, the embodiment of FIGS. 6a, 6b and 6c contains a central screw 225 that can be turned by the top dial portion 201 for a continuous dose adjustment device. As the screw 225 is turned, the maximum depression of the button 201 of increased or decreased as the screw 225 moves the button 201 toward or away from the dosing control collar 3. As with the embodiment of FIGS. 1a-1d, 2, 4, 5a and 5b, a sensor 20 or other smart chip may be arranged to detect the rotation and hence the dosage amount.

Figure 7A:
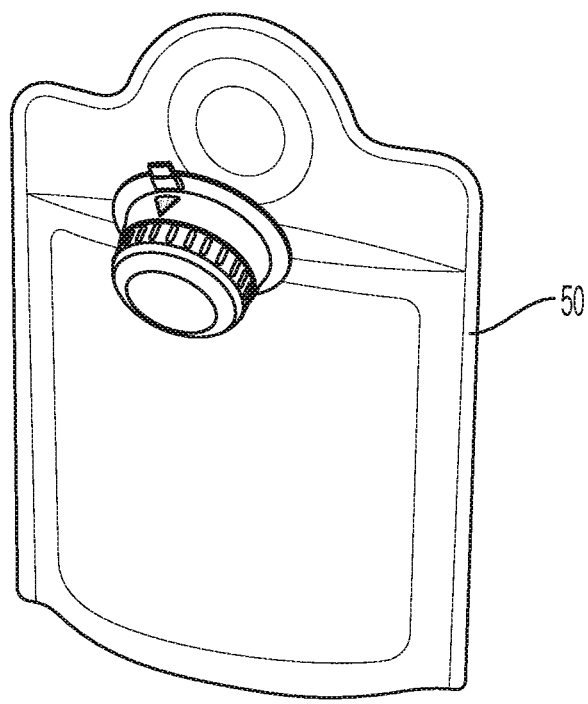
FIG. 7a is a perspective view of an adjustable fluid dosing dispenser according to an embodiment of the invention proximate to a matching opening in a flexible fluid container.
Figure 7B:
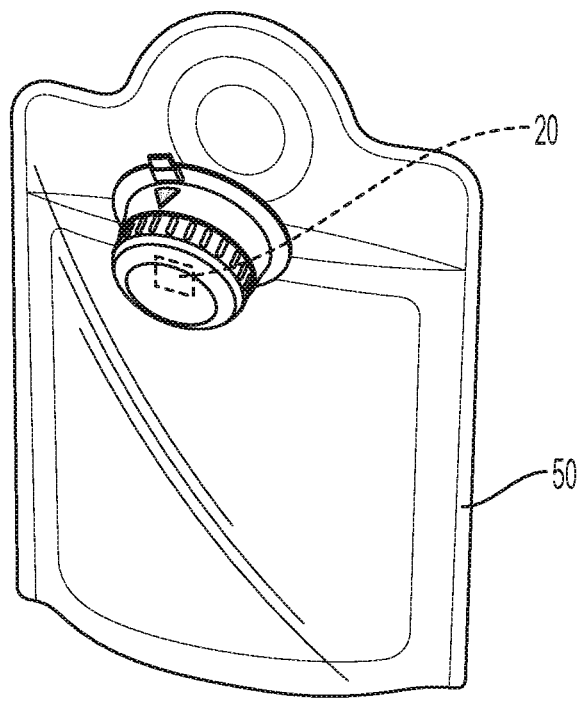

FIGS. 7a and 7b show the adjustable metering device of the invention about to be connected to a flexible fluid container 50, preferably a bag or pouch. According to a preferred embodiment, the fluid container 50 is collapsible as fluid is dispensed therefrom and preferably contains no air. According to one embodiment, the bottom of the adjustable metering device has an adhesive that makes a secure and air-tight connection to the fluid container 50. According to a further embodiment, the adhesive may be covered prior to use with a thin pull-away film to protect and preserve the adhesive until it is time to connect the device to the fluid container 50. According to various alternative embodiments, the bottom of the adjustable metering device may be heat welded to the fluid container 50, sonic welded to the fluid container 50, or sealed to the fluid container 50 in any other known method. According to a further embodiment, the fluid container 50 may have a reinforced region and/or treated surface that corresponds to the shape and size of the device to facilitate strong and secure connection and prevent container breaking or tearing should a force or load be applied to the device after it has been attached to the fluid container 50.

Figure 8A:
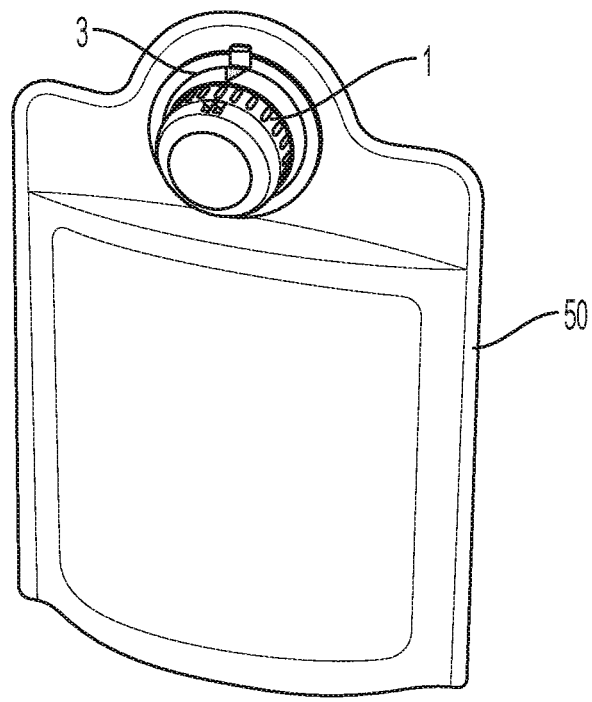
FIG. 8a is a perspective view of an adjustable fluid dosing dispenser attached to the surface of a flexible fluid container according to an embodiment of the invention.
Figure 8B:
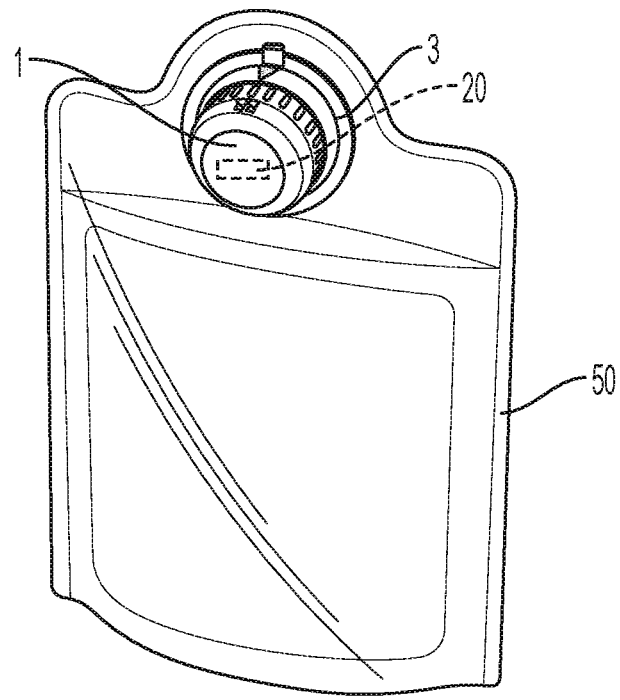

FIGS. 8a and 8b show an adjustable metering device of the invention connected to a flexible fluid container 50. The device can be operated to dispense fluid no matter the orientation of the device in space, as it is agnostic to gravity or other forces except for the depression of the dial/button 1.

Referring now to FIGS. 9-10, further embodiments of the present invention are shown, wherein an adjustable fluid dispensing device may be dispensed without physical depression of the flexible dosing dome. In FIGS. 9-10, a non-mechanical, digital fluid dispensing device for dispensing fluid is shown. Unlike the dispensing device of the previous embodiments, dispensing of a fluid is accomplished using a touch sensor 320 within button 301, which may be, for example, a 5-wire resistive touch sensor, a surface capacitive touch sensor, a projective capacitive touch sensor, a surface acoustic wave sensor, an infrared touch technology sensor, or any other touch sensor known in the art. Upon physical contact with button 301, touch sensor 320 signals movement of the flexible dosing dome 302 downward to evacuate the interior volume of the dome 302 via the fluid outlet 310 and subsequently allows the flexible dosing dome 302 to return to its original shape, thereby drawing fluid into the interior of the dome 302 under vacuum action. Thus, the fluid dispensing device of the present embodiment requires less force to dispense fluid than the mechanical fluid dispensing device of the previous embodiment. In some embodiments, the digital fluid dispensing device also requires no physical depression of the button 301 against the flexible dosing dome 302 to reload or ready the fluid dispensing device of the present embodiment. Button 301 may be of integral construction with dosing control collar 303 as shown in FIG. 9 or may be of separate construction as depicted in FIG. 10, where the button 301 includes an annular projection 325 which is complimentarily fit within channel 317 formed between collar 303 and dosing dome 302, so as to be removeable or replaceable.

In either of the digital embodiments depicted in FIGS. 9-10, the fluid dispensing device may include further digital features, which may include use touch sensor 320 to select the maximum depression of dosing dome 302. In these embodiments, button 301 may include a GUI in which a user may select incremental amounts of doses, which may include a half or partial dose. After making a selection, the sensor 320 signals a maximum depression of the dosing dome 302 to deliver a dose which corresponds to the selection made by an end user and is less than a single dose of fluid.

Figure 11:
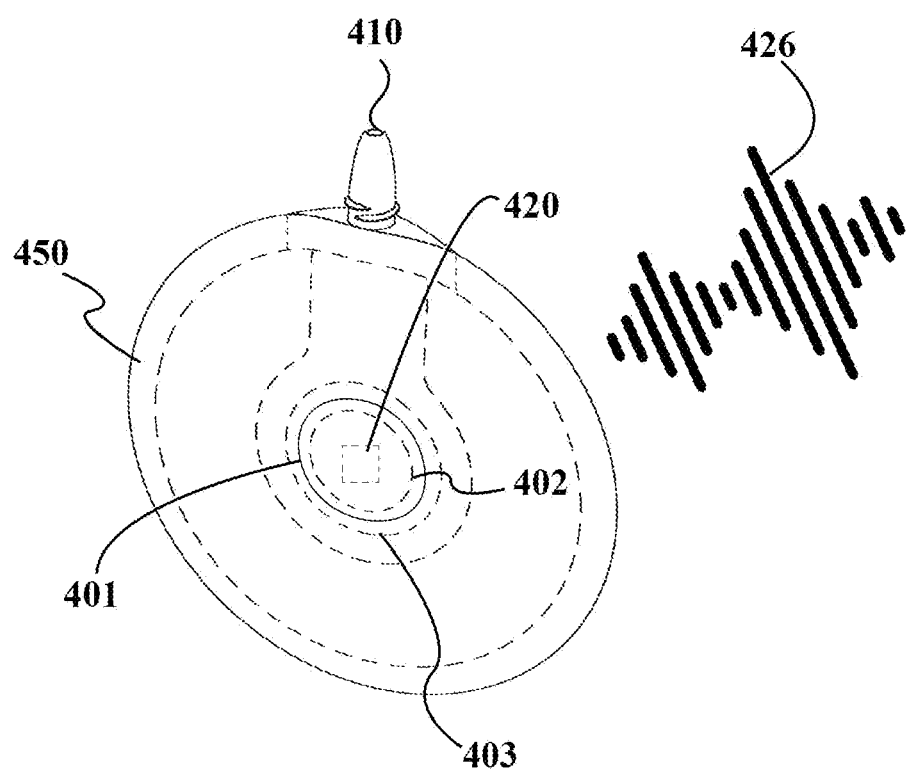
FIG. 11 is a perspective view of an embodiment of the fluid dispensing device of the present invention.

In some embodiments, the actuation of the digital dispensing device is voice-activated, as shown in FIG. 11. In these embodiments, one or more sensors 420 may comprise a sound sensor, for example an in-built capacitive microphone, a peak detector and an amplifier, or other similar devices known in the art. Sound sensor 420 is designed to respond to voice commands 426 to actuate the fluid dispensing device, wherein the dose within the interior of dome 402 is evacuated, delivered via the fluid outlet 410, and a new dose is readied within the interior of the dome 402. In these embodiments, the sound sensor 420 may be capable of recording specific voice commands 426 which are then required to be received to sound sensor 420 before a dose may be dispensed. In some embodiments, voice commands 426 may also change the volume of the dose delivered via fluid outlet 410 and/or transmit information regarding the dose or amount of fluid within 450 to one or more devices wirelessly for the purposes of tracking dose information, reporting malfunctions/proper operation of the fluid dispensing device, or reordering. The sound sensor 420 may require the voice commands 426 to be of a specific frequency in order to prevent misuse of the fluid dispensing device or accidental/premature dispensing of a dose within the fluid dispensing device.

Figure 12:
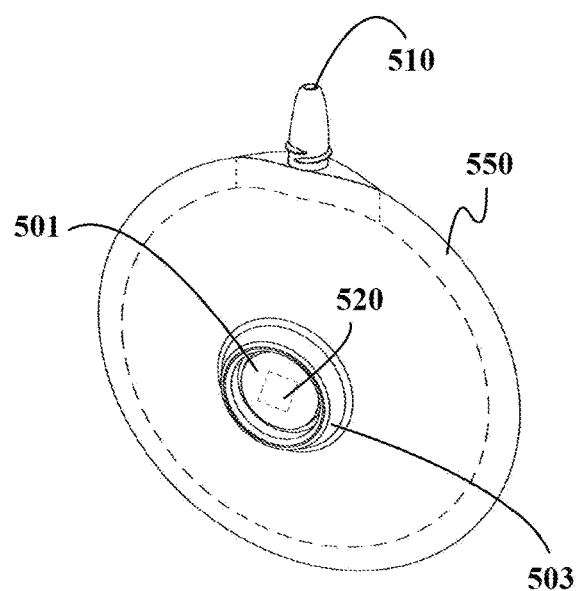
FIG. 12 is a perspective view of an embodiment of the fluid dispensing device of the present invention.
Figure 13:
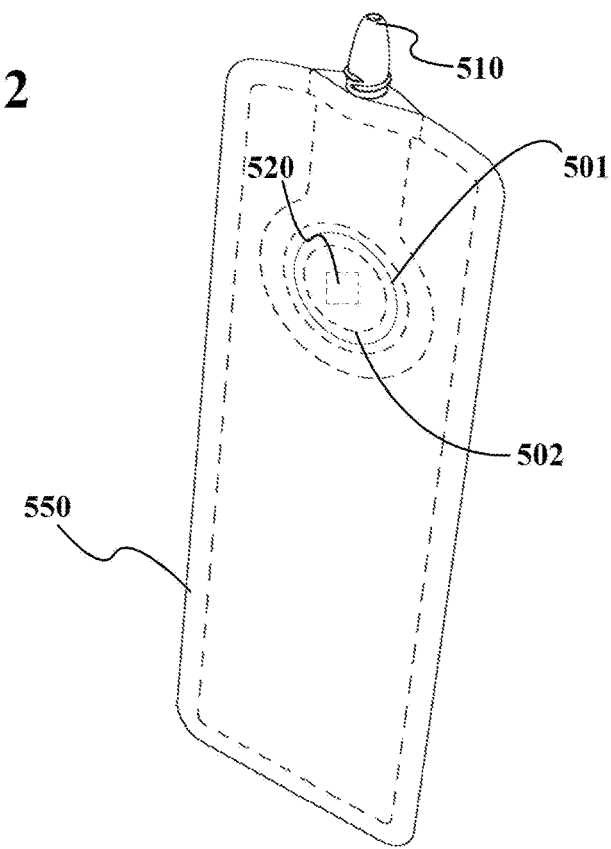
FIG. 13 is a perspective view of an embodiment of the fluid dispensing device of the present invention.

In an embodiment depicted in FIGS. 12 and 13, the fluid dispensing device may include a sensor which may be utilized for adjusting, dispensing, or readying a metered volume of fluid to be dispensed through a biometric identification and/or administration. In these embodiments, the biometric sensor 520 is designed to detect an end user through facial recognition, fingerprint recognition, or any other biometric sensing technology which is known in the art. The fluid dispensing device of the present embodiment may be mechanically actuated through depression of the button 501 only upon the biometric validation described above. In the event that the biometric validation procedure is not met, the fluid dispensing device will remain inoperable, and depression of the button 501 will not dispense a dose. Alternatively, the fluid dispensing device may dispense a dose of fluid automatically or digitally without any mechanical depression. In such embodiments, after biometric validation procedures are met by biometric sensor 520, the procedures to operate fluid dispensing device begin, thereby causing evacuation of flexible dosing dome (not shown), delivery of a dose via the fluid outlet 510, and reloading of a dose by readying flexible dosing dome.

In any of the above embodiments, one or more components of the fluid dispensing device may be constructed of sustainable, or organic-based materials. These sustainable materials may cardboard, paper, wood, compostable and biodegradable plastic alternatives, or any other similar of any suitable non-plastic polymer which may be of rigid or semi-rigid construction, such as cardboard, paper, wood, cornstarch, mycelium, agar, cotton, tapioca or any similar compostable and/or biodegradable material known in the art. These sustainable materials are suitable for use in lamination, layering, or reacting with other rigid, or semi-rigid materials for optimum functional, or tactile operation of the fluid dispensing device.

In another embodiment depicted in FIGS. 14-23, the mechanical and digital fluid dispensing devices of the previous embodiments may contain include the sustainable materials on the exterior of the flexible container, thereby providing additional protection to flexible container. In an embodiment shown in FIGS. 14 and 15, the fluid dispensing device of one or more of the previous embodiments is shown, comprising a substantially rectangular pouch 50' having exposed on an upper surface the upper portion of dispensing collar 3' and dosing dome 2'. Dispensing port or nozzle 10' is connected to outlet channel (not shown) to dispense the fluid contents of the flexible container 50' in a metered fashion. Exterior covers of substantially the same dimensions as the flexible container are attached to the upper and lower surfaces of flexible container 50a', 50b', respectively. Cover 605a includes an opening 652 sized to permit at least dosing dome 2' to be accessed from the exterior. Covers 605a, b may be made of soft and partially flexible sustainable materials that are more rigid than the layers used for flexible container 50', but still sufficient to bend, for example, when placed in a user's pocket. During assembly, heat or any suitable adhesive may be used to laminate or otherwise secure exterior covers 605a, 605b to the flexible container. The sides of the flexible container 50' may remain exposed, including the end for dispensing nozzle 10'. Alternatively, only one of exterior cover 605a or 605b may be used, and the other side of flexible container 50' left exposed, or one or both of exterior covers 605a, 605b may cover less than all of a side of the flexible container 50'.

Figure 16:
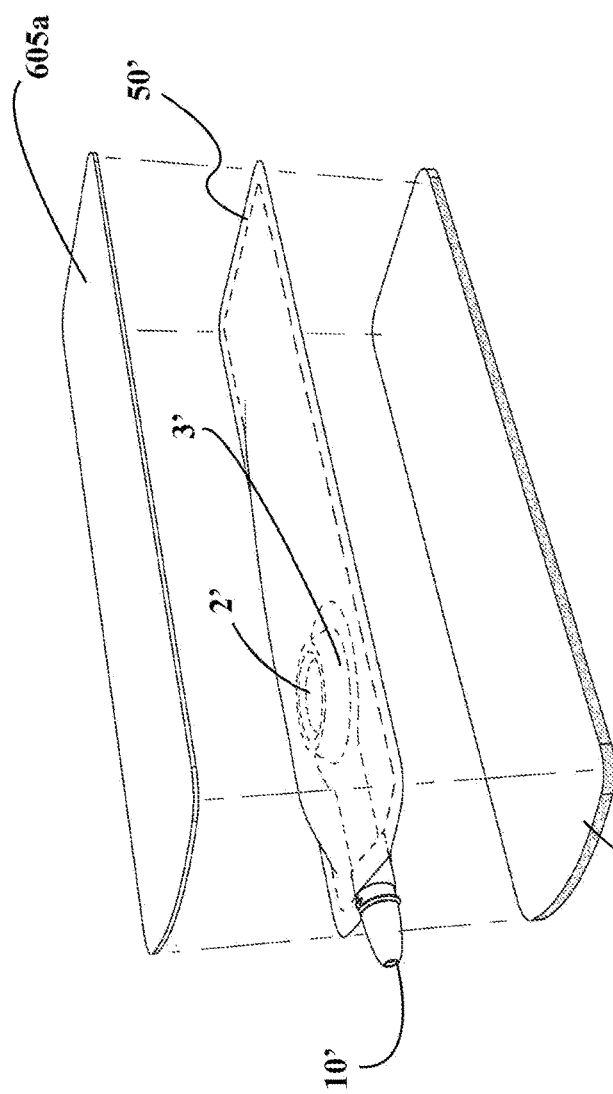
FIG. 16 is an exploded view of an embodiment of the fluid dispensing device of the present invention.
Figure 17:
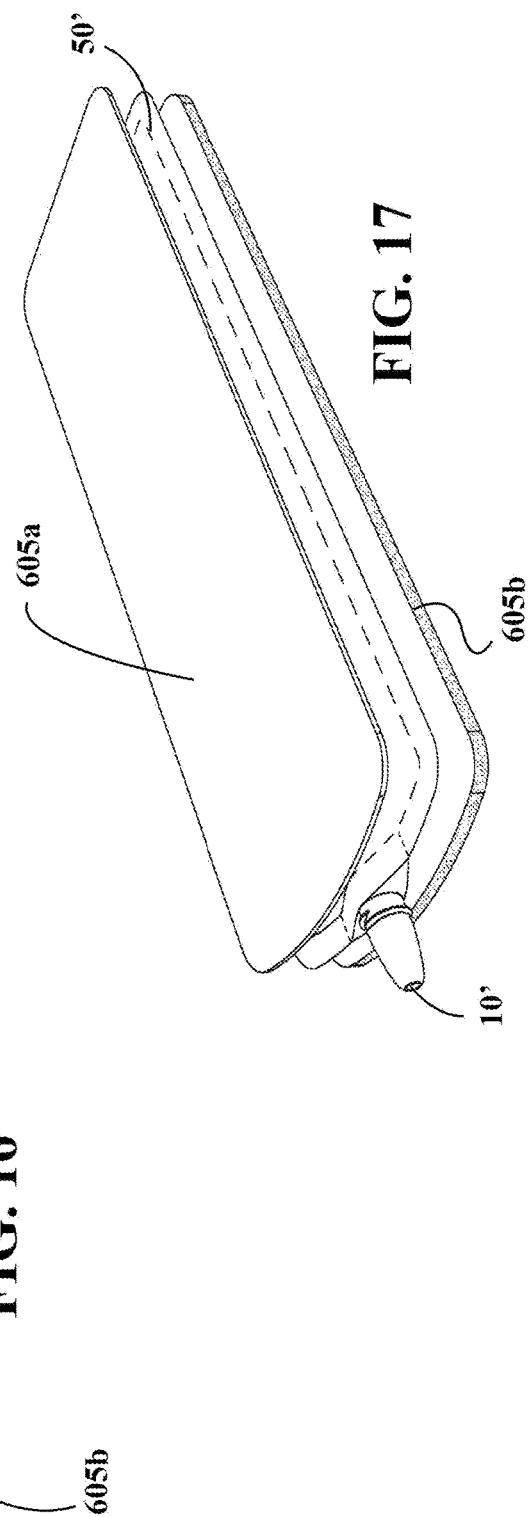
FIG. 17 is a perspective view of an embodiment of the fluid dispensing device of the present invention.
Figure 21:
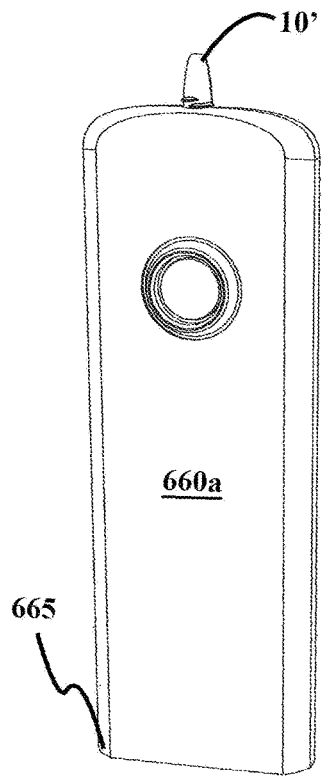
FIG. 21 is a perspective view of an embodiment of the fluid dispensing device of the present invention.
Figure 22:
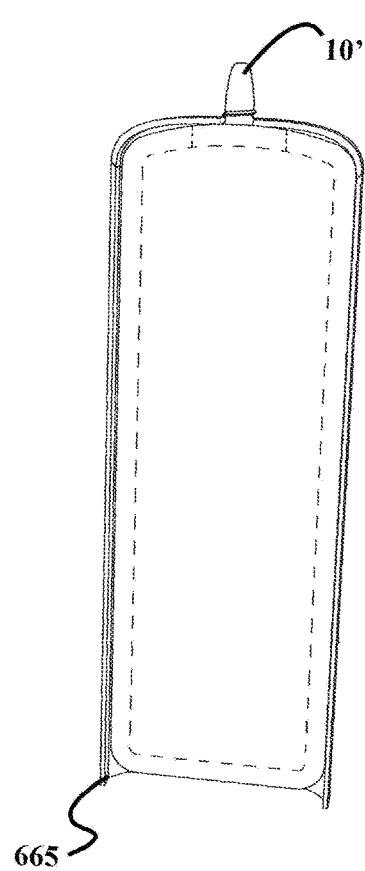
FIG. 22 is a side plan view of the embodiment of the fluid dispensing device shown in FIG. 21.
Figure 23:
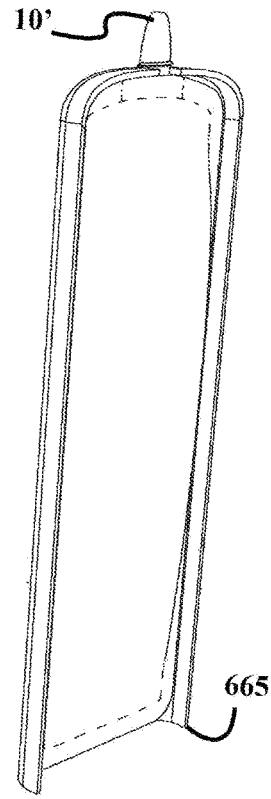
FIG. 23 is a perspective view of the embodiment of the fluid dispensing device shown in FIG. 21.

An alternative to the soft and partially flexible covers of FIGS. 14-15 is shown in FIGS. 16-17, where both covers 605a,b have no openings therein. However, cover 605a may still sufficiently flexible to permit the user to push through the cover at a marked location and depress dome build 102 thereunder. In other embodiments utilizing the digital dispensing device of the previous embodiments, cover 605a may be include the touch sensor, biometric sensor, or sound sensor (not shown) of the previous embodiments to allow dosing of the fluid dispensing device without physical depression.

Instead of these soft and partially flexible covers, the present invention may utilize rigid or semi-rigid cases as shown in FIGS. 18-20. In FIG. 18, an open-bottom case 660a made of sustainable materials having more rigidity than the previous covers is fitted over the upper side of the flexible container 50a'. Case 660a has opening 662 aligned with collar 3' and dosing dome 2'. Side walls 661 are provided around the periphery to cover the sides edges of container 50', except for notch 664 for nozzle 10'. After assembly, the flexible container 50' is secured to and nested within cover 660a, as shown in the inverted view of FIG. 19. In the assembled view of FIG. 20, the upper portion of dispensing collar 3' and dosing dome 2' are exposed and extend through opening 662, and nozzle 10' extends through notch 664.

Any of the covers 605a, 605b or case 660a may be configured with flat, squared-off ends so that the covered or encased container 50' may be stood up on end on top of a flat surface, such as a table or shelf. For example, in FIGS. 21-23, case 660a has flat end 665 which permits the fluid dispensing device to be placed in a stable upright position with the dispensing nozzle 10' pointed upwards, for user functionality and storage.

While the covers 605a, 605b and cases 660a are shown configured for a substantially rectangular pouch 50' in FIGS. 14-23, they may be configured to correspond to and fit containers of different configurations, such as circular or triangular.

In any of the previous embodiments, the sensor 20 or smart chip of the fluid dispensing device may be used to learn and anticipate the dispensing features of the previous embodiments. In these embodiments, the sensor 20 may utilize artificial intelligence analysis and feedback to predict the timing of fluid dosing, the amount of fluid dosing, or other performance tasks of the previous embodiments. In one example, the sensor 20 may record or transmit wirelessly tracked data information based on the habits and/or performances of the fluid dispensing device to set reminders, forecast functionality, and/or communicates next steps, which could include reordering, location prediction to facilitate delivery, or other functionalities which may be necessary.

Application will represent educational materials on the fluid being dispensed.

Compliance measured by actual pressure on the button 1 and number of times pushed. Time and date captured. Ability to reorder when pouch is close to deletion.

Smartphone application automatically track the dose size and time using either the mechanical or sensor technologies.

Data can be shared with physician, pharmacy, retailers, manufacturers or others, as permissible by users, requiring compliance, monitoring and reordering capabilities. Sensor 20 and app technologies allow for identification of reorder options using GPS technologies or online ordering applications.

According to an embodiment the fluid can be of any viscosity.

According to another embodiment RFID, sensor stickers, Bluetooth and other sensor technologies are used.

The user will download the app. The app will pick up the sensor signal from the sensor technology and prompt for educational and compliance engagement.

The app will automatically capture dose, time of dose, prompt for next dose, and alert when near depletion, requiring a reorder.

This is doable from day one using readily available sensor technologies.

The app will alert when the dose is due.

Pressure sensor 20 in the "button" sends a signal that the fluid was dispensed and how much. 1 TOUCH dispensing technology indicates dosage.

Patient can provide permissions through the app to share with physician, pharmacy, retailers, manufacturers or others requiring compliance, monitoring and reordering capabilities.

Sensor technologies provide automatic tracking to ensure ease of use. GPS enables real-time capabilities for reorder and retail opportunities.

While the present invention has been particularly described, in conjunction with one or more specific embodiments, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. An apparatus for dispensing fluid, comprising:
a flexible and collapsible fluid container;
a fluid dispenser pump connected to the flexible and collapsible fluid container configured to draw fluid from the flexible and collapsible fluid container into the fluid dispenser pump and to dispense fluid through a fluid delivery channel to an exit port upon actuation of the pump,
the dispenser pump having an actuator comprising a dose delivery button connected to said flexible and collapsible fluid container via a dose button base which, upon depression by an end user, actuates the fluid dispenser pump to dispense a dose of fluid;
a biometric sensor located in the apparatus for validating the end user, whereupon the dispenser pump is actuated upon physical contact and depression of the dose delivery button by the end user.

2. The apparatus of claim 1, wherein the apparatus is configured to remain inoperable, and depression of the button does not dispense the dose, without the biometric sensor validates the end user.

3. The apparatus of claim 1, wherein the apparatus is configured to measure dose compliance by the end user by pressure exerted on the button when depressed by the end user and a number of times the button is depressed by the end user.

4. The apparatus of claim 3, wherein the apparatus is configured to transmit dose compliance data to a smartphone for tracking compliance of the end user.

5. A smartphone that is configured to receive the compliance data from the apparatus of claim 4 and determine one or more of a next dosage time and when to reorder the fluid.

6. The smartphone of claim 5, configured to determine the next dosage time and prompt the end user to administer the next dose at the next dosage time.

7. The apparatus of claim 1, including: a graphical user interface for selecting an incremental dose amount; and a touch sensor that limits depression motion of the button to correspond with the selected dose amount.

8. A method of dispensing fluid dispensed from an apparatus comprising:
providing a flexible and collapsible fluid container, a fluid dispenser pump connected to the flexible and collapsible fluid container configured to draw fluid from the flexible and collapsible fluid container into the fluid dispenser pump and to dispense fluid through a fluid delivery channel to an exit port upon actuation of the pump,
the dispenser pump having an actuator comprising a dose delivery button connected to said flexible and collapsible fluid container via a dose button base which, upon depression by a user, actuates the fluid dispenser pump to dispense a dose of fluid, and including
a biometric sensor located in the apparatus for validating an end user, whereupon the fluid dispenser pump is actuated upon physical contact and depression of the dose delivery button by the end user;
contacting, by the user, the dose delivery button;
signaling the sensor to actuate the fluid dispensing pump; and
dispensing the fluid from the flexible and collapsible fluid container through the exit port.

9. The method of claim 8, comprising the apparatus remaining inoperable, and depression of the button not dispensing the dose, without the biometric sensor validating the end user.

10. The method of claim 8, comprising the apparatus measuring dose compliance by the end user by pressure exerted on the button when depressed by the end user and a number of times the button is depressed by the end user.

11. The method of claim 10, comprising the apparatus transmitting dose compliance data to a smartphone for tracking compliance of the end user.

12. The method of claim 11, comprising the smartphone receiving the compliance data from the apparatus and determining one or more of a next dosage time and when to reorder the fluid.

13. The method of claim 12, including the smartphone determining the next dosage time and prompting the end user to administer the next dose at the next dosage time.

14. The method of claim 8, including selecting via a graphical user interface an incremental dose amount; and limiting by a touch sensor a depression motion of the button to correspond with the selected dose amount.

15. A fluid dispensing apparatus comprising:
a cylindrical base unit having a flat and continuous bottom surface, a top surface having a raised circumferential wall, and a center area;
a flexible dosing dome configured to sit inside the center area of said base unit to form a pump chamber;
said bottom surface of said base unit having a fluid inlet opening to said pump chamber to permit the flow of fluid there-through, said base also defining a fluid delivery channel between said pump chamber and a fluid delivery outlet opening on an outside surface of said base unit;
a combination dial and button having the shape of a cylinder with a closed top and open bottom, a bottom portion of said combination dial and button configured to sit inside a channel defined by said base unit top surface and said flexible dome, said button including a Graphical User Interface in communication with a sensor to select by an end user a dose amount of fluid to be dispensed; and
a biometric sensor located in the apparatus for validating the end user, whereupon the pump chamber is actuated upon physical contact and depression of the dose delivery button by the end user.

16. The apparatus of claim 15, wherein the apparatus is configured to remain inoperable, and depression of the button does not dispense the dose, without the biometric sensor validates the end user.

17. The apparatus of claim 15, wherein the apparatus is configured to measure dose compliance by the end user by pressure exerted on the button when depressed by the end user and a number of times the button is depressed by the end user.

18. The apparatus of claim 17, wherein the apparatus is configured to transmit dose compliance data to a smartphone for tracking compliance of the end user.

19. A smartphone that is configured to receive the compliance data from the apparatus of claim 18 and determine one or more of a next dosage time and when to reorder the fluid.

20. The smartphone of claim 19, configured to determine the next dosage time and prompt the end user to administer the next dose at the next dosage time.

21. The apparatus of claim 15, including a touch sensor that limits depression motion of the button to correspond with the selected dose amount.

* * * * *